US00PP14854P2

(12) United States Plant Patent
Sakazaki

(10) Patent No.: US PP14,854 P2
(45) Date of Patent: Jun. 1, 2004

(54) VERBENA PLANT NAMED 'USBENAL11'

(50) Latin Name: *Verbena hybrida*
Varietal Denomination: USBENAL11

(75) Inventor: Ushio Sakazaki, Shiga (JP)

(73) Assignee: Plant 21 LLC, San Marco, CA (US)

( * ) Notice: Subject to any disclaimer, the term of this patent is extended or adjusted under 35 U.S.C. 154(b) by 0 days.

(21) Appl. No.: 10/638,692

(22) Filed: Aug. 11, 2003

(51) Int. Cl.[7] ..... A01H 5/00
(52) U.S. Cl. ..... Plt./308
(58) Field of Search ..... Plt./308

(56) References Cited
PUBLICATIONS

UPOV ROM GTITM Computer Database, GTI JOUVE Retrieval Software 2003/05 Citation for 'USBENAL11'.*
http://www.provenwinners.com/catalog/details.php?ID=807.*

* cited by examiner

*Primary Examiner*—Bruce R. Campell
*Assistant Examiner*—W C Haas
(74) *Attorney, Agent, or Firm*—C. A. Whealy

(57) ABSTRACT

A new and distinct cultivar of Verbena plant named 'USBENAL11', characterized by its semi-upright and outwardly spreading plant habit; vigorous growth habit; large light violet-colored flowers; and resistance to Powdery Mildew.

1 Drawing Sheet

Botanical classification/cultivar designation: *Verbena hybrida* cultivar USBENAL11.

BACKGROUND OF THE INVENTION

The present Invention relates to a new and distinct cultivar of Verbena plant, botanically known as *Verbena hybrida*, and hereinafter referred to by the name 'USBENAL11'.

The new Verbena is a product of a planned breeding program conducted by the Inventor in Hikone, Shiga, Japan. The objective of the breeding program is to develop new disease-resistant and high temperature-tolerant Verbena cultivars with semi-upright plant habit and attractive flower coloration.

The new Verbena originated from a cross-pollination made by the Inventor on Apr. 20, 1999 of an unknown selection of *Verbena hybrida*, not patented, as the female, or seed, parent with an unnamed proprietary selection of *Verbena hybrida*, not patented, as the male, or pollen, parent. The cultivar USBENAL11 was discovered and selected by the Inventor as a flowering plant within the progeny from this cross-pollination in a controlled environment in Bonsall, Calif. on Jun. 10, 2000.

Asexual reproduction of the new cultivar by cuttings taken at Bonsall, Calif., since Jun. 20, 2000, has shown that the unique features of this new Verbena are stable and reproduced true to type in successive generations of asexual reproduction.

SUMMARY OF THE INVENTION

The following traits have been repeatedly observed and are determined to be the unique characteristics of 'USBENAL11'. These characteristics in combination distinguish 'USBENAL11' as a new and distinct cultivar:

1. Semi-upright and outwardly spreading plant habit.
2. Vigorous growth habit.
3. Large light violet-colored flowers.
4. Resistant to Powdery Mildew.

In side-by-side comparisons conducted in Hikone, Shiga, Japan, plants of the new Verbena differed from plants of the female parent selection in the following characteristics:

1. Plants of the new Verbena were not as upright as plants of the female parent selection.
2. Plants of the new Verbena were more vigorous than plants of the female parent selection.
3. Plants of the new Verbena were resistant to Powdery Mildew whereas plants of the female parent selection were susceptible to Powdery Mildew.

In side-by-side comparisons conducted in Hikone, Shiga, Japan, plants of the new Verbena differed from plants of the male parent selection primarily in flowering time as plants of the new Verbena flowered earlier than plants of the male parent selection.

The new Verbena can be compared to the cultivar, Temari Blue, not patented. However, in side-by-side comparisons conducted in Bonsall, Calif., plants of the new Verbena differed from plants of the cultivar Temari Blue in the following characteristics:

1. Plants of the new Verbena were more upright than plants of the cultivar Temari Blue.
2. Plants of the new Verbena flowered earlier than plants of the cultivar Temari Blue.
3. Plants of the new Verbena had larger flowers than plants of the cultivar Temari Blue.

BRIEF DESCRIPTION OF THE PHOTOGRAPHS

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Verbena.

The photograph at the top of the sheet comprises a side perspective view of three typical plants of 'USBENAL11' grown in a container.

The photograph at the bottom of the sheet is a close-up view of typical flowers and leaves of 'USBENAL11'.

DETAILED BOTANICAL DESCRIPTION

In the following description, color references are made to The Royal Horticultural Society Colour Chart, 1995 Edition, except where general terms of ordinary dictionary significance are used. Plants grown in 15-cm containers with three plants per container were used for the aforementioned photographs and following description. Plants were about four weeks from planting rooted cuttings. Plants were grown under conditions which closely approximate commercial production conditions during the spring in Bonsall, Calif. in an outdoor nursery. During the production period, day temperatures ranged from about 18 to about 35° C. and night temperatures ranged from about 7 to about 18° C.

Botanical classification: *Verbena hybrida* cultivar USBENAL11.

Parentage:

*Female parent.*—Unknown selection of *Verbena hybrida*, not patented.

*Male parent.*—Unnamed proprietary selection of *Verbena hybrida*, not patented.

Propagation:

*Type cutting.*—Vegetative tip cuttings.

*Time to initiate roots.*—About 7 days at 18° C.

*Time to develop roots.*—About 21 days at 18° C.

*Root description.*—Fibrous; whitish in color.

*Rooting habit.*—Freely branching.

Plant description:

*General appearance.*—Semi-upright and outwardly spreading plant habit; eventually somewhat trailing plant habit.

*Growth and branching habit.*—Freely basal branching; about three lateral branches develop per plant. Pinching, that is, removal of the terminal apices, enhances branching with lateral branches potentially forming at every node. Vigorous growth habit; moderate growth rate.

*Plant height.*—About 18 cm.

*Plant diameter or spread* (*single plant*).—About 20 cm by 28 cm.

*Lateral branch description.*—Length: About 26 cm. Diameter: About 2.5 mm. Internode length: About 5.5 to 7.5 cm. Texture: Pubescent. Color: 144A.

*Foliage description.*—Arrangement: Opposite, simple. Length: About 4.5 cm. Width: About 2.8 cm. Shape: Deltoid. Apex: Broadly acute. Base: Attenuate. Margin: Crenate, irregular. Texture, upper and lower surfaces: Pubescent; coarse. Venation pattern: Pinnate. Color: Developing foliage, upper surface: 146A. Developing foliage, lower surface: 147B. Fully expanded foliage, upper surface: 147A; venation, 146D. Fully expanded foliage, lower surface: 147B; venation, 147D. Petiole: Length: About 1 cm. Diameter: About 2 mm. Texture, upper and lower surfaces: Pubescent. Color, upper and lower surfaces: 147D.

Flower description:

*Flower type and habit.*—Single upright salverform flowers arranged on hemispherical corymbs. Freely flowering with about 24 flowers per inflorescence. Inflorescences positioned above and beyond the foliage. Flowers last about four to five days under greenhouse conditions. Corollas not persistent. Flowers not fragrant.

*Flowering season.*—In the garden, flowering is continuous from spring until fall.

*Inflorescence height.*—About 3.5 to 4 cm.

*Inflorescence diameter.*—About 5 cm.

*Flower size.*—Diameter: About 2 cm by 2 cm. Height (depth): About 2.3 cm.

*Flower buds.*—Length: About 1.8 mm. Diameter: About 3 mm. Shape: Elongate. Color: 92A.

*Petals.*—Quantity/arrangement: Five per flower fused at base. Lobe length: About 9 mm. Lobe width: About 7 mm. Shape: Roughly cordate. Apex: Emarginate. Margin: Entire. Texture, upper and lower petal surfaces: Glabrous, smooth; velvety. Texture, throat and tube: Pubescent. Color: When opening, upper surface: 84A. When opening, lower surface: Lighter than 85A. Fully opened, upper surface: Brighter than 85A; towards throat, 155D; color becoming closer to 85B to 85C to 85D with development. Fully opened, lower surface: 85B to 85C. Throat: Close to 157A. Tube: Close to 157A.

*Sepals.*—Quantity/arrangement: Five, fused into an elongated tube. Length: About 1.6 cm. Diameter: About 1 mm. Shape: Linear. Apex: Acute. Margin: Entire. Texture, upper and lower surfaces: Pubescent. Color, upper surface: 146B. Color, lower surface: 146A.

*Peduncles.*—Length: About 4.5 to 5 cm. Diameter: About 1.5 mm. Strength: Strong. Angle to stem: Upright to about 45° from vertical. Texture: Pubescent. Color: 144B.

*Reproductive organs.*—Stamens: Quantity: Four per flower. Anther shape: Oval. Anther length: Less than 1 mm. Anther color: 1A. Pollen amount: Scarce. Pollen color: 1A. Pistils: Quantity: One per flower. Pistil length: About 1.8 cm. Style length: About 1.6 cm. Style color: 144D. Stigma shape: Parted. Stigma color: 144A. Ovary color: 144B.

*Seed/fruit.*—Seed and fruit production has not been observed.

Disease/pest resistance: Plants of the new Verbena have been observed to be resistant to Powdery Mildew. Plants of the new Verbena have not been observed to be resistant to other pathogens and pests common to Verbena.

Temperature tolerance: Plants of the new Verbena have been observed to be tolerant to temperatures ranging from −4 to 40° C.

It is claimed:

1. A new and distinct cultivar of Verbena plant named 'USBENAL11', as illustrated and described.

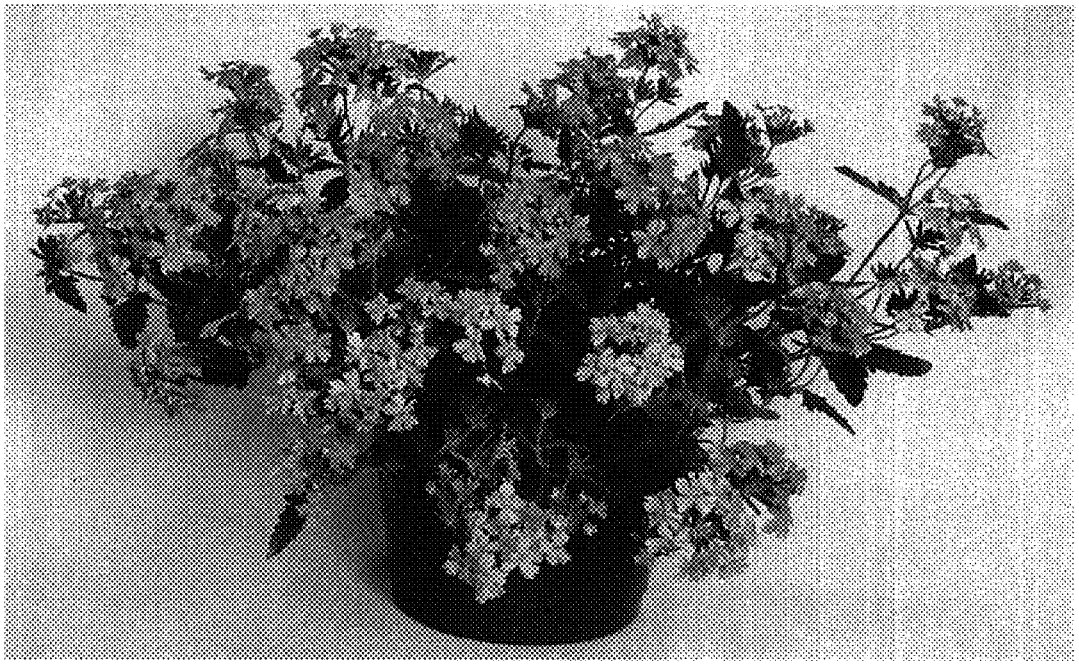
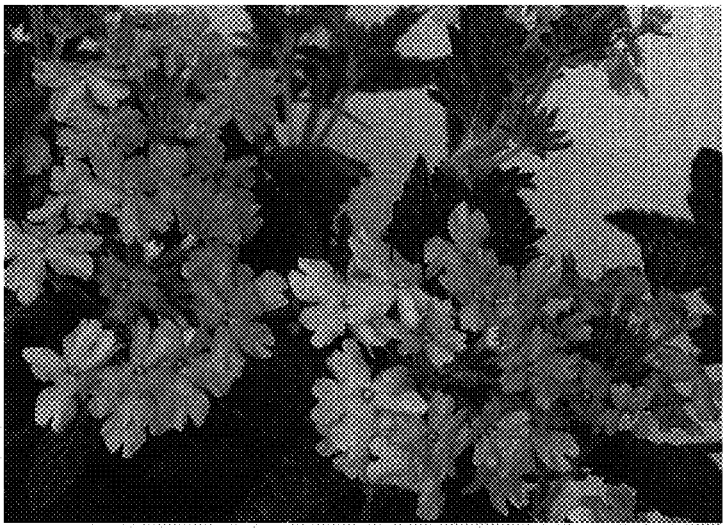

* * * * *